US008096164B2

(12) United States Patent
Koehler

(10) Patent No.: US 8,096,164 B2
(45) Date of Patent: Jan. 17, 2012

(54) APPARATUS AND METHODS FOR MANAGEMENT OF FLUID CONDITION

(75) Inventor: Don Koehler, Mentor, OH (US)

(73) Assignee: Trico Corporation, Pewaukee, WI (US)

( * ) Notice: Subject to any disclaimer, the term of this patent is extended or adjusted under 35 U.S.C. 154(b) by 450 days.

(21) Appl. No.: 12/321,172

(22) Filed: Jan. 16, 2009

(65) Prior Publication Data

US 2009/0199617 A1 Aug. 13, 2009

Related U.S. Application Data

(60) Provisional application No. 61/021,638, filed on Jan. 17, 2008.

(51) Int. Cl.
*G01N 19/02* (2006.01)
(52) U.S. Cl. .......................................................... 73/10
(58) Field of Classification Search ........................ 73/10
See application file for complete search history.

(56) References Cited

U.S. PATENT DOCUMENTS

| | | | |
|---|---|---|---|
| 126,624 A | 5/1872 | Coffee |
| 539,117 A | 5/1895 | Busch |
| 779,357 A | 1/1905 | Gardner |
| 805,645 A | 11/1905 | Guillott |
| 992,503 A | 5/1911 | Howard |
| 1,113,276 A | 10/1914 | Woodmansee |
| 1,571,495 A | 2/1926 | Smith |
| 1,600,262 A | 9/1926 | Wickham |
| 1,610,283 A | 12/1926 | Hill |
| 1,687,395 A | 10/1928 | Shew |
| 1,688,279 A | 10/1928 | Locke |
| 1,864,195 A | 6/1932 | Hall |
| 2,227,646 A | 1/1941 | Hillman |
| 2,335,557 A | 11/1943 | Winther |
| 2,340,455 A | 2/1944 | Davis |
| 2,376,623 A | 5/1945 | Romberg |
| 2,397,597 A | 4/1946 | Dunkle |
| 2,439,709 A | 4/1948 | Ashbury |

(Continued)

FOREIGN PATENT DOCUMENTS

CA 2291763 7/2002

(Continued)

OTHER PUBLICATIONS

International Search Report, dated Jan. 20, 1999 for PCT/US98/09039, International Filing Date May 8, 1998.

(Continued)

*Primary Examiner* — Hezron E Williams
*Assistant Examiner* — Mark A Shabman
(74) *Attorney, Agent, or Firm* — Ryan Kromholz & Manion, S.C.

(57) ABSTRACT

A method is provided for invoking condition monitoring and predicting parametric equipment and lube condition among a plurality of machines; relying on individual or multiple machine and or lube combinations; comprising establishing a based routine accepting information from multiple sources to simultaneously calculate and compare measured and projected conditions relative to parameters selected to be critical; including multiple condition monitoring techniques like: lube analysis, vibration analysis, thermography, ultrasound and equipment lube monitoring techniques whereas parameters monitored are variables and a specific parametric value represents condition or a group of variables together represents a condition; said variables are not to be confused with attribute data indicating pass/fail without identifying a specific parametric value. The process outputs the specific parameter and days to exceed specified condemning limit for each combination of equipment and lube selected.

1 Claim, 18 Drawing Sheets

U.S. PATENT DOCUMENTS

| | | |
|---|---|---|
| 2,589,081 A | 3/1952 | Hertz |
| 2,608,993 A | 9/1952 | Andrews |
| 2,703,628 A | 3/1955 | Pompeo et al. |
| 2,774,621 A | 12/1956 | Kilbourne, Jr. |
| 2,930,432 A | 3/1960 | Engstrom |
| 2,950,943 A | 8/1960 | Forrest |
| 2,995,213 A | 8/1961 | Gross |
| 3,123,095 A | 3/1964 | Kohler |
| 3,193,990 A | 7/1965 | Smith |
| 3,233,173 A | 2/1966 | Lees et al. |
| D205,166 S | 6/1966 | Price |
| 3,323,291 A | 6/1967 | Kern |
| 3,338,262 A | 8/1967 | Chopelin |
| 3,447,562 A | 6/1969 | Hoffman |
| D217,665 S | 5/1970 | Self |
| D217,666 S | 5/1970 | Self |
| D217,667 S | 5/1970 | Self |
| 3,952,566 A | 4/1976 | Jacobson |
| 4,018,579 A | 4/1977 | Hofmann |
| 4,047,814 A | 9/1977 | Westcott |
| 4,058,766 A | 11/1977 | Vogel et al. |
| 4,064,455 A | 12/1977 | Hopkins et al. |
| 4,105,092 A | 8/1978 | Zeidler et al. |
| 4,227,419 A | 10/1980 | Park |
| 4,312,424 A | 1/1982 | Taylor et al. |
| 4,345,668 A | 8/1982 | Gaunt |
| 4,423,371 A | 12/1983 | Senturia et al. |
| 4,445,168 A | 4/1984 | Petryszyn |
| 4,466,508 A | 8/1984 | Buse |
| 4,503,383 A | 3/1985 | Agar |
| D279,549 S | 7/1985 | Elmburg |
| 4,527,661 A | 7/1985 | Johnstone et al. |
| 4,591,024 A | 5/1986 | Erickson |
| 4,629,334 A | 12/1986 | Hochstein |
| 4,646,070 A | 2/1987 | Yashuhara |
| 4,681,189 A | 7/1987 | Krisiloff |
| 4,689,553 A | 8/1987 | Haddox |
| 4,733,556 A | 3/1988 | Meitzler et al. |
| 4,735,286 A | 4/1988 | Miki et al. |
| 4,738,336 A | 4/1988 | Smith et al. |
| 4,990,057 A | 2/1991 | Rollins |
| 5,025,222 A | 6/1991 | Scott et al. |
| 5,039,425 A | 8/1991 | Caris et al. |
| 5,045,798 A | 9/1991 | Hendrick |
| 5,060,760 A | 10/1991 | Long et al. |
| 5,071,527 A | 12/1991 | Kauffman |
| 5,072,190 A | 12/1991 | Martin |
| 5,080,195 A | 1/1992 | Mizumoto et al. |
| 5,101,936 A | 4/1992 | Paredes et al. |
| 5,103,181 A | 4/1992 | Gaisford et al. |
| 5,125,480 A | 6/1992 | Gregory et al. |
| D333,177 S | 2/1993 | Poirier |
| 5,196,898 A | 3/1993 | Tamura et al. |
| 5,197,569 A | 3/1993 | Roessler et al. |
| 5,200,027 A | 4/1993 | Lee et al. |
| 5,203,680 A | 4/1993 | Waldrop |
| D336,509 S | 6/1993 | Safford et al. |
| D336,679 S | 6/1993 | Safford et al. |
| 5,224,051 A | 6/1993 | Johnson |
| D338,158 S | 8/1993 | Poirier |
| 5,249,455 A | 10/1993 | Cox |
| 5,260,665 A | 11/1993 | Goldberg et al. |
| 5,262,732 A | 11/1993 | Dickert et al. |
| 5,269,175 A | 12/1993 | Chmiel et al. |
| 5,271,528 A | 12/1993 | Chien |
| 5,273,134 A | 12/1993 | Hegemier et al. |
| 5,274,335 A | 12/1993 | Wang et al. |
| 5,314,613 A | 5/1994 | Russo |
| 5,317,252 A | 5/1994 | Kranbuehl |
| 5,318,152 A | 6/1994 | Ehlert |
| 5,328,275 A | 7/1994 | Winn et al. |
| 5,330,636 A | 7/1994 | Reichert |
| 5,332,064 A | 7/1994 | Liu |
| 5,334,941 A | 8/1994 | King |
| 5,381,874 A | 1/1995 | Hadank et al. |
| 5,382,942 A | 1/1995 | Raffa et al. |
| D358,097 S | 5/1995 | Leibowitz |
| D358,548 S | 5/1995 | Platte |
| 5,457,396 A | 10/1995 | Mori et al. |
| 5,499,902 A | 3/1996 | Rockwood |
| 5,504,573 A | 4/1996 | Cheiky-Zelina |
| 5,521,515 A | 5/1996 | Campbell |
| 5,540,086 A | 7/1996 | Park et al. |
| 5,542,499 A | 8/1996 | Westermeyer |
| 5,548,217 A | 8/1996 | Gibson et al. |
| 5,568,842 A | 10/1996 | Otani |
| 5,596,266 A | 1/1997 | Mori et al. |
| 5,604,441 A | 2/1997 | Freese |
| 5,614,830 A | 3/1997 | Dickert et al. |
| 5,634,531 A | 6/1997 | Graf et al. |
| 5,647,735 A | 7/1997 | Rockwood |
| 5,656,767 A | 8/1997 | Garvey, III et al. |
| 5,671,825 A | 9/1997 | Wong et al. |
| 5,674,401 A | 10/1997 | Dickert et al. |
| 5,702,592 A | 12/1997 | Suri et al. |
| 5,754,055 A | 5/1998 | McAdoo et al. |
| 5,779,005 A | 7/1998 | Jones, Jr. et al. |
| 5,789,665 A | 8/1998 | Voelker et al. |
| 5,806,630 A | 9/1998 | Bernal |
| 5,816,212 A | 10/1998 | Lindquist et al. |
| 5,824,889 A | 10/1998 | Park et al. |
| 5,826,986 A | 10/1998 | Adkins et al. |
| 5,858,070 A | 1/1999 | Halm et al. |
| 5,878,842 A | 3/1999 | Rake |
| 5,884,802 A | 3/1999 | Leibowitz |
| 6,028,433 A | 2/2000 | Cheiky-Zelina et al. |
| 6,077,330 A | 6/2000 | Sabelstrom |
| 6,113,676 A | 9/2000 | Kumpulainen |
| 6,192,025 B1 | 2/2001 | Chen |
| 6,204,656 B1 | 3/2001 | Cheiky-Zelina et al. |
| 6,223,589 B1 | 5/2001 | Dickert et al. |
| 6,250,152 B1 | 6/2001 | Klein et al. |
| 6,253,601 B1 | 7/2001 | Wang et al. |
| 6,273,031 B1 | 8/2001 | Verdegan et al. |
| 6,277,173 B1 | 8/2001 | Sadakata et al. |
| 6,278,282 B1 | 8/2001 | Marszalek |
| 6,368,411 B2 | 4/2002 | Roberson, Jr. et al. |
| 6,443,006 B1 | 9/2002 | Degrave |
| 6,447,573 B1 | 9/2002 | Rake |
| 6,449,580 B1 | 9/2002 | Bardetsky et al. |
| 6,459,995 B1 | 10/2002 | Collister |
| 6,460,656 B1 | 10/2002 | Jones, Jr. et al. |
| 6,509,749 B1 | 1/2003 | Buelna et al. |
| 6,513,368 B2 | 2/2003 | Bondarowicz et al. |
| 6,519,034 B1 | 2/2003 | Engler et al. |
| 6,535,001 B1 | 3/2003 | Wang |
| 6,551,055 B2 | 4/2003 | Rockwood |
| 6,553,812 B2 | 4/2003 | Park et al. |
| 6,557,396 B2 | 5/2003 | Ismail et al. |
| 6,564,126 B1 | 5/2003 | Lin et al. |
| 6,568,919 B1 | 5/2003 | Fletcher et al. |
| D485,189 S | 1/2004 | Montalbano et al. |
| 6,851,676 B2 | 2/2005 | Martins et al. |
| 6,932,856 B2 | 8/2005 | Rake |
| 7,017,712 B1 | 3/2006 | Rake et al. |
| D527,639 S | 9/2006 | Voss et al. |
| D528,425 S | 9/2006 | Van Dorin et al. |
| 7,140,468 B2 | 11/2006 | Rake et al. |
| D573,885 S | 7/2008 | Considine et al. |
| D589,597 S | 3/2009 | Bloch et al. |
| D589,807 S | 4/2009 | Gundrum et al. |
| D589,808 S | 4/2009 | Gundrum et al. |
| D589,809 S | 4/2009 | Gundrum et al. |
| 7,541,004 B2 | 6/2009 | Niksa et al. |
| 2002/0178780 A1* | 12/2002 | Van Mullekom et al. ........ 73/10 |

FOREIGN PATENT DOCUMENTS

| | | |
|---|---|---|
| CA | 2289726 | 3/2003 |
| CA | 122622 | 4/2009 |
| CA | 127725 | 5/2009 |
| CA | 127726 | 5/2009 |
| CA | 1271724 | 5/2009 |
| DE | 37325 | 3/1968 |
| GB | 121092 | 12/1918 |
| JP | 2-308916 | 12/1990 |
| JP | 411132304 | 5/1999 |

OTHER PUBLICATIONS

Iotech Catalog, p. 65, Jan. 1995.
"Model 958PF On-Line Ferrograph", *Foxboro Analytical*, (no month available) 1980, 4 pgs.
958F Series On-Line Ferrograph Installation and Operation, The Foxboro Company, (no month available) 1980, 6 pgs.
"Journal Reprints", The British Institute of Non-Destructive Testing, M.H. Jones and A.R. Massoudi, Insight, vol. 37 No. 8, Aug. 1995. pp. 606-610.
"Basics of Measuring the Dielectric Properties of Materials", Hewlett Packard, (no month available) 1992, No. 1217-1.
"The Nist 60-Millimeter Diameter Cylindrical Cavity Resonator: Performance Evaluation for Permittivity Measurements", Eric J. Vanzura, Richard G. Geyer and Michael D. Janezic, Aug. 1993, National Institute of Standards and Technology Technical Note.
Measuring Moisture in Liquids; A New Method, *Sensors*, Dec. 1996 pp. 42-47.
Sensor Mediated in Situ Measurement of Moisture in Organic Liquids, Phys-Chem Scientific Corp. sales literature, date unknown.
"Hydraulic and Lubrication Systems Solutions: Water Sensor—An Essential tool for fluid condition monitoring" Pall Corporation sales literature, date unknown.
Environmental Solutions for the Military: Pall Portable Fluid Purifier, not dated; Pall Corporation web site address: www.pall.com/environ/miltary/solutions/products/purifier.html.
Pall Water Sendor: An essential tool for fluid condition monitoring; Pall Corporation sales literature, date unknown.
"Advancement of PREDICT/DLI Industrial Sensors", M.A. Cheiky-Zelina, R.W. Brown and D.E. Schuele, Department of Physics, Case Western Reserve University, Mar. 1997.
Filtration Products, Solutions for Tomorrow's Challenges, Trico sales literature, 7 pages, date unknown.
Mobile Filtration System, Oil Service Products sales literature, 1 page, date unknown.
Mobile Filtration Systems, Schroeder Industries LLC, 2 pages, date unknown.

* cited by examiner

| Component Type | SPID Count | Sample Count |
|---|---|---|
| Compressor/Gas | 1 | 1 |
| Mixer | 1 | 1 |
| Radiator | 1 | 1 |
| Sump | 1 | 1 |
| Mill | 2 | 2 |
| Transmission | 2 | 2 |
| Variable Speed Drive | 2 | 3 |
| Hydraulic/Axial | 1 | 4 |
| Generator/Diesel | 2 | 4 |
| Turbine/Steam | 2 | 4 |
| Feeder | 1 | 5 |
| Lube Test | 1 | 5 |
|  | 1 | 6 |
| Hydraulic/Power | 3 | 6 |
| Combustion Turbine | 4 | 6 |
| Filter | 5 | 10 |
| Tank | 4 | 14 |
| Fan/Forced Draft | 3 | 17 |
| Engine/Diesel | 8 | 19 |
| Blower | 13 | 20 |
| Pump/Motor | 5 | 22 |
| Oil Filter | 1 | 24 |
| Compressor/Centrifuge | 3 | 29 |
| Drive | 4 | 46 |
| Coal Mill | 4 | 64 |
| Fan/Ind. Draft | 8 | 76 |
| Engine | 5 | 93 |
| Centrifuge | 19 | 104 |
| Unknown | 23 | 104 |
| Generator/Turbine/Gearbox | 4 | 108 |
| Control System | 9 | 120 |
| Steam Turbine | 6 | 123 |
| Air Heater | 12 | 154 |
| Generator | 24 | 171 |
| Turbine/Generator | 14 | 205 |
| Lube Oil System | 27 | 256 |
| Feed Pump | 9 | 258 |
| Pulverizer | 21 | 287 |
| Hydraulic | 48 | 294 |
| Gear Reducer | 53 | 296 |
| Gearcase/Speed Reducer | 33 | 341 |
| Compressor | 21 | 362 |
| Motor | 61 | 439 |
| Turbine | 47 | 457 |
| Fan | 43 | 696 |
| Bearings | 69 | 728 |
| Pump | 76 | 738 |
| Reservoir | 40 | 773 |
| Gearcase | 305 | 1864 |
| TOTAL SPIDS | 1014 | |
| TOTAL COMPONENTS | 49 | |

| Component | Units |
|---|---|
| Pump | 56 |
| Fan | 33 |
| Reservoir | 33 |
| Bearings | 26 |
| Motor | 26 |
| Lube Oil System | 21 |
| Centrifuge | 16 |
| Feed Pump | 8 |
| Fan/Ind. Draft | 7 |
| Unknown | 7 |
| Air Heater | 6 |
| Compressor | 6 |
| Turbine | 6 |
| Gear Reducer | 4 |
| Pump/Motor | 4 |
| Compressor/Centrifuge | 3 |
| Engine/Diesel | 3 |
| Fan/Forced Draft | 3 |
| Gearcase | 3 |
| Hydraulic | 3 |
| Drive | 2 |
| Diesel Engine 4 Stroke | 1 |
| Mixer | 1 |
| Engine | 1 |
| TOTAL | 279 |

Fig. 5

| SPID | Name | Days to Limit | Parameter | Sampled Level | Projected Level | Limit Value | Average Sampling Frequency (days) | Last Sample Date | Calculated Parameters | Projection Points | Component Type | SPID Description | Lube Name |
|---|---|---|---|---|---|---|---|---|---|---|---|---|---|
| 21806? | 79E03327 | -191 | Direct Reading WPC | 985 | 1773 | 811 | 162 | 5/17/2007 | 8 | 3 | Gearcase | Conveyor C2 Gear Reducer | Synthagear EP ISO 220 |
| 21800 | 76E09950 | | | | | | | 5/10/2007 | | | Gearcase | WI Collector Conveyor Gear Reducer | Gear Compound EP ISO 220 |
| 21803 | 76E05212 | | | | | | | 6/10/2007 | | | Gearcase | WI Conveyor 3 Gear Reducer | Gear Compound EP ISO 220 |
| 21807? | 76E06699 | | | | | | | 8/10/2007 | | | Gearcase | WI Transfer Conveyor Gear Reducer | Gear Compound EP ISO 220 |
| 21806? | 76E08736 | | | | | | | 5/10/2007 | | | Gearcase | WI Conveyor 2 Gear Reducer | Gear Compound EP ISO 220 |
| 21866 | 76E06674 | | | | | | | 4/24/2007 | | | Gearcase | WI Conveyor 1 Gear Reducer | Gear Compound EP ISO 220 |
| 21861 | 16E07.24 | | | | | | | 4/23/2007 | | | Gearcase | WI Belt Feeder BF1 Gear Reducer | Synthagear EP ISO 220 |
| 21858 | 79E17733 | | | | | | | 7/14/2006 | | | Gearcase | Conveyor LC1 Gear Reducer | Synthagear EP ISO 220 |
| 21851 | 79E17751 | | | | | | | 7/14/2006 | | | Gearcase | Conveyor LC3 Gear Reducer | Synthagear EP ISO 220 |
| 21864 | 79E17752 | | | | | | | 7/14/2006 | | | Gearcase | Conveyor LC4 Gear Reducer | Synthagear EP ISO 220 |
| 17306 | 71E16036 | 686 | Direct Reading WPC | 414 | 432 | 811 | 37 | 10/24/2007 | 6 | 17 | Gearcase | 1A Air Heater Drive Gearbox | Meshgear 629 ISO 150 |
| 21800 | 79E03336 | 736 | Direct Reading WPC | 291 | 376 | 811 | 152 | 5/17/2007 | 8 | 3 | Gearcase | Conveyor BF1B Gear Reducer | Synthagear EP ISO 220 |
| 21865 | 76E02630 | 2753 | ROE Silicon PPM | 130 | 166 | 811 | 162 | 5/17/2007 | 8 | 3 | Gearcase | Belt Feeder BF1B Gear Reducer | Synthagear EP ISO 220 |
| 21867 | 76E02630 | 4412 | ROE Silicon PPM | 7 | 10 | 100 | 161 | 5/17/2007 | 8 | 3 | Gearcase | Belt Feeder BF1A Gear Reducer | Synthagear EP ISO 220 |
| 17306? | 71E15037 | 6519 | Titrator TAN mg KOH/g. | 0.47 | 0.44 | 0.00 | 36 | 10/24/2007 | 6 | 17 | Gearcase | 1B Air Heater Drive Gear Box | Meshgear 629 ISO 150 |
| 21866 | 79E03333 | 161.47 | ROE Silicon PPM | 3 | 4 | 100 | 162 | 5/17/2007 | 8 | 3 | Gearcase | Conveyor C1 Gear Reducer | Synthagear EP ISO 220 |
| 21072 | 79E02031 | 22539 | ROE Tin PPM | 0 | 0 | 15 | 164 | 10/31/2007 | 8 | 4 | Gearcase | Coal Breaker CBB Gear Reducer | Synthagear EP ISO 220 |
| 8677! | 71E12987 | 4901 | ROE Silicon PPM | 0 | 3 | 100 | 80 | 1/22/2006 | 6 | 15 | Gearcase | 7A Conveyor Gearbox | Meshgear 629 ISO 150 |
| 21807! | 79E03333 | 76399 | ROE Copper PPM | 1 | 1 | 130 | 164 | 10/31/2007 | 8 | 4 | Gearcase | Coal Breaker CBA Gear Reducer | Synthagear EP ISO 220 |

Fig. 7

SPID Limit Set Report for limitsetid 190: TURBINE ALLEGHENY TEST DEK.

Limits:

| Test Id | Test | Upper Trigger | Upper Limit | Upper Recommendation | Lower Trigger | Lower Limit | Lower Recommendation |
|---|---|---|---|---|---|---|---|
| 20 | Titrator Karl Fischer PPM | High Alarm | 1500.00000000 | | | | |
| 21 | Titrator TAN mg KOH/g | High Alarm | 1.07000000 | | | | |
| 61 | Particle Count Number of Particles >6 microns Particles/ml | High Alarm | 25001.000000000 | | | | |
| 62 | Particle Count Number of Particles >14 microns Particles/ml | High Alarm | 321.00000000 | | | | |
| 01 | Viscometer Viscosity at 40°C cSt | High Alarm | 31.52000000 | | Low Alarm | 25.56400000 | |

Edit Projection Options

Test Projection to Limit

Perform limitset Statistical Distribution Analysis by Sample Point 

Calculate Limits

| Lube Name | MFG Name | SPID Count | Sample Count |
|---|---|---|---|
| Cylinder Oil W ISO 460 | Chevron | 1 | 1 |
| DTE AA ISO 320 | Mobil | 1 | 1 |
| Meropa 320 FM | Texaco | 1 | 1 |
| Permagear EP 680 | Amoco | 1 | 1 |
| Chevron 460 | Chevron | 1 | 2 |
| AIO 100 | Chevron | 2 | 2 |
| Gear Compound EP ISO 150 | Chevron | 2 | 2 |
| Turbo T32 | Shell | 2 | 2 |
| Amokon 46 | Amoco | 2 | 3 |
| AIO 220 | Chevron | 3 | 3 |
| American Industrial ISO 68 | Chevron | 4 | 4 |
| Ultra Gear Lubricant ISO 220 | Chevron | 1 | 5 |
| Omala Gear ISO 220 | Shell | 2 | 10 |
| Chevron 150 | Chevron | 2 | 12 |
| Mobilgear SHC 460 ISO 460 | Mobil | 1 | 16 |
| DTE 797 Oil ISO 32 | Mobil | 1 | 17 |
| SHC 630 ISO 220 | Mobil | 3 | 17 |
| Gear Compound EP ISO 220 | Chevron | 11 | 17 |
| Almasol 608 Gear Lubricant | lcation Engr | 1 | 18 |
| Almasol 605 Gear Lubricant | lcation Engr | 4 | 28 |
| Multilec 6805 | cation Engr | 2 | 32 |
| Omala Gear ISO 320 | Shell | 4 | 40 |
| Mobilgear 632 ISO 320 | Mobil | 7 | 41 |
| Monolec Turbine Oil 6406 ISO | cation Engr | 6 | 42 |
| Unknown | | 22 | 42 |
| Ultra Gear Lubricant ISO 460 | Chevron | 15 | 47 |
| Ultra Gear Lubricant ISO 320 | Chevron | 29 | 61 |
| Gear Compound EP ISO 680 | Chevron | 37 | 63 |
| Gear Compound EP ISO 150 | Chevron | 23 | 66 |
| Gear Compound EP ISO 460 | Chevron | 15 | 67 |
| Synthogear EP ISO 220 | Amoco | 27 | 97 |
| Gear Compound EP ISO 320 | Chevron | 59 | 191 |
| Mobilgear 629 ISO 150 | Mobil | 12 | 230 |
| Mobilgear 634 ISO 460 | Mobil | 33 | 703 |
| TOTAL LUBES IN GEAR CASES | | 34 | |

Fig. 12A

| MFG Name | Model | SPID Count | Sample Count |
|---|---|---|---|
| General Electric | Unknown | 1 | 3 |
| Lightnin Mixer | Unknown | 6 | 11 |
| Foote Bros. | L2245c326u | 1 | 14 |
| Foote Bros. | L2245c-326u | 1 | 14 |
| Foote Bros. | L2245C326u | 1 | 14 |
| Foote-Jones | MNL723B284T | 1 | 14 |
| Falk | MN2090FZ2A | 1 | 15 |
| Horsburgh & Scott | sn-600226 | 1 | 15 |
| Dresser | 7B15H15 | 1 | 16 |
| Foote-Jones | L2245c326u | 1 | 16 |
| Foote-Jones | MN727L SN-419737 | 1 | 16 |
| Foote-Jones | mn8z55sl | 1 | 16 |
| Foote-Jones | mnhyp hu-770 | 1 | 16 |
| Foote-Jones | mnhyphu-770 | 1 | 16 |
| Foote-Jones | mnl723b256t | 1 | 16 |
| Foote-Jones | MNLK726C405u | 1 | 16 |
| Foote-Jones | sn-315218-99 | 1 | 16 |
| Line-O-Power | mn8273l-5d715371 | 1 | 16 |
| Line-O-Power | mn627bsl-445u | 1 | 16 |
| Lufkin | 58/3317921 | 1 | 16 |
| Lufkin | sn-129 | 1 | 16 |
| Lufkin | sn 130 | 1 | 16 |
| Lufkin |  | 1 | 16 |
| None | 1x43290 | 1 | 16 |
| Philadelphia Gear | 10h2 sn-51539230 | 1 | 16 |
| Philadelphia Gear | 4H8Z SN-514281 | 1 | 16 |
| Philadelphia Gear | 8HL2-SN515350 | 1 | 16 |
| Power Tech Foote Jones | sn-0c63548 | 1 | 16 |
| (Not Provided) | Unknown | 11 | 18 |
| Falk | Unknown | 16 | 36 |
| Falk | MN6-532727-7A | 1 | 40 |
| Falk | MN6-5327277 | 1 | 42 |
| Combustion Engineering | rps rp size 823863 | 1 | 43 |
| Combustion Engineering | RPS, RP size 823863 | 1 | 43 |
| Combustion Engineering | RPS, RP size 823 86 | 1 | 43 |
| Combustion Engineering | RPS RP size 823863 | 1 | 44 |
| Babcock & Wilcox | mps-89 | 1 | 45 |
| Altra |  | 29 | 50 |
| Combustion Engineering | rps, rp size 823, 863 | 2 | 87 |
| Babcock & Wilcox | MPS-89 | 4 | 183 |
|  |  | 45 | 245 |
| (Not Provided) |  | 118 | 545 |
|  | TOTAL Gearcase | 265 | |
|  | TOTAL GEARCASE TYPES | 42 | |

Fig. 12B

| MFG Name | Model | SPID Count | Sample Count |
|---|---|---|---|
| Foote-Jones | MNL723B284T | 1 | 14 |
| Foote-Jones | L2245c326u | 1 | 16 |
| Foote-Jones | MN727L SN-419737 | 1 | 16 |
| Foote-Jones | mn8z55sl | 1 | 16 |
| Foote-Jones | mnhyp hu-770 | 1 | 16 |
| Foote-Jones | mnhyphu-770 | 1 | 16 |
| Foote-Jones | mnl723b256t | 1 | 16 |
| Foote-Jones | MNLK726C405u | 1 | 16 |
| Foote-Jones | sn-315218-99 | 1 | 16 |
| TOTAL Foote-Jones | | 9 | |

*Fig. 13A*

| Lube Name | MFG Name | SPID Count | Sample Count |
|---|---|---|---|
| DTE AA ISO 320 | Mobil | 1 | 1 |
| Mobilgear 634 ISO 460 | Mobil | 4 | 64 |
| Mobilgear 629 ISO 150 | Mobil | 5 | 77 |
| TOTAL LUBES | | 3 | |

*Fig. 13B*

SPID Limit Set Report for limitsetId 188: Test Set Gearbox.

Limits:

| Test Id | Test | Upper Trigger | Upper Limit | Upper Recommendation | Lower Trigger | Lower Limit | Lower Recommendation |
|---|---|---|---|---|---|---|---|
| 1 | RDE Iron PPM | High Alarm | 599.00000000 | | | | |
| 2 | RDE Chromium PPM | High Alarm | 15.00000000 | | | | |
| 4 | RDE Copper PPM | High Alarm | 136.00000000 | | | | |
| 5 | RDE Lead PPM | High Alarm | 67.00000000 | | | | |
| 6 | RDE Tin PPM | High Alarm | 15.00000000 | | | | |
| 9 | RDE Silicon PPM | High Alarm | 5.00000000 | | | | |
| 21 | Titrator TAN mg KOH/g | High Alarm | 0.82000000 | | | | |
| 193 | Direct Reading MPC | High Alarm | 811.00000000 | | | | |

Edit Projection Options

Test Projection to Limit

Perform Limitset Statistical Distribution Analysis by Sample Point

Calculate Limits

Fig. 14

| SPID | Name | Days to Limit | Parameter | Sampled Level | Projected Level | Limit Value | Average Sampling Frequency (days) | Last Sample Date | Parameters Calculated | Projection Points |
|---|---|---|---|---|---|---|---|---|---|---|
| 86811 | 71E12892 | 0 | RDE Silicon PPM | 11 | 9 | 5 | 90 | 3/26/2007 | 8 | 16 |
| 86783 | 71E13220 | 0 | Direct Reading WPC | 61 | 1211 | 811 | 90 | 3/26/2007 | 8 | 16 |
| 86809 | 71E12890 | 0 | Direct Reading WPC | 903 | 1013 | 811 | 90 | 3/26/2007 | 8 | 16 |
| 86820 | 71E12900 | >270 | RDE Silicon PPM | 1 | 2 | 5 | 90 | 3/26/2007 | 8 | 16 |
| 86784 | 71E13225 | >365 | RDE Silicon PPM | 2 | 2 | 5 | 90 | 3/26/2007 | 8 | 16 |
| 86821 | 71E12896 | >365 | Titrator TAN mg KOH/g | 0.455 | 0.550 | 0.832 | 108 | 3/26/2007 | 8 | 12 |
| 86773 | 71E12912 | >365 | RDE Lead PPM | 1 | 1 | 87 | 90 | 3/26/2007 | 8 | 16 |
| 86777 | 71E13076 | >365 | RDE Tin PPM | 0 | 0 | 15 | 97 | 12/22/2006 | 8 | 14 |
| 86782 | 71E13208 | >365 | RDE Lead PPM | 0 | 0 | 87 | 90 | 3/26/2007 | 8 | 16 |

APPARATUS AND METHODS FOR MANAGEMENT OF FLUID CONDITION

RELATED APPLICATION

This application claims the benefit of copending provisional patent application Ser. No. 61/021,638 filed 17 Jan. 2008.

BACKGROUND OF THE INVENTION

Lubrication is an important aspect of maintaining machinery in proper operating condition. Machine elements such as bearings, journals, shafts, and joints require proper lubrication between their moving surfaces to decrease friction, prevent contamination, reduce wear and dissipate heat. Improper lubrication is likely to lead to premature component wear and component or system failure.

When determining the optimal lubrication between moving machine elements, many factors should be considered. These factors include the mode of operation of the machine, the type of machine element to be lubricated, the environment of the machine, the operating speed of the machine, the lubricant's viscosity, the lubricant's temperature, the lubricant's ingredients, and the lubricant's condition.

Prior art lubricators, such as the TRICO OptoMatic oiler, supply a constant level of lubricant within a lubricant reservoir to a machine element. The lubricant level is predetermined for the particular application and cannot be changed during the operating time of the machine to which the constant level lubricator is attached. Although this type of lubricator provides reasonable performance in many steady-state operations, multiple variables can create unacceptable operating conditions and lead to premature wear, or even failure, of machine elements. The variables include "on" and "off" operating modes (machine cycling), oil viscosity, machine speed, lubricant temperature, lubricant condition, and lubricant vessel pressure.

Other prior art devices indicate by LED signals the status of the equipment's lubrication such as lubricant condition within acceptable levels, lubricant condition at the upper limit of acceptable levels, and lubricant condition immediate action required. These devices are effective because an operator is signaled only when the lubricant condition is at the upper limit of acceptable levels or if immediate action is required. This reduces maintenance costs and productivity is enhanced.

Available condition monitoring techniques including lubricant analysis, vibration monitoring, thermography, ultrasonic and others collect information specific to existing equipment or lubricant condition measured by one or multiple parameters. The condition is treated as a single point analysis or combined with historical monitoring event to establish a trend either through simply connecting specific parametric values or mathematically calculating a historical trend including the present value. Values are individually compared manually or automatically.

Selected maintenance monitoring software routines may include selected condemning limits either automatically or manually selected. These systems will aid in identifying equipment conditions exceeding limits.

Lubricants typically degrade during operation and exposure to environmental conditions. Degradation also occurs as lubricant protective additives are consumed or break down. Condemning limits can be set for various physical and chemical properties of lubricating oil, which represent criteria of the lubricant that are measured during usage of the lubricant. If condemning limits are met, ordinarily the lubricant is either rehabilitated through a rehabilitation sequence, or changed altogether.

Available systems are limited in that they do not simultaneously analyze all parameters identifying the parameter at highest risk of exceeding the condemning limits and therefore cannot project condition to the future. Available systems do not identify the time to exceed condemning limits. Available systems do not identify the specific parameters causing individual equipment/lubricant combinations or groups of similar characteristics to exceed condemning limits. Available systems do not identify systematic parameters causing multiple equipment/lubricant combinations within a group to exceed condemning limits. These systems do not use virtual condemning limit sets containing elements from multiple sources creating a complete limit set. Available systems do not automatically generate condemning limits based on historical values and condition ratings. Available systems do not do not allow individual parameters in a multiple parameter analysis to be individually calculated using liner or quadratic trend routines.

Limitations of existing systems force equipment owner and managers to direct maintenance based on limited information, which reduces monitoring program effectiveness and limits planning capability.

It is desired to have increased predictability in forecasting when adverse conditions might occur in lubrication systems.

SUMMARY OF THE INVENTION

The systems and methods of the present invention relate generally to the field of lubrication and specifically to the field of devices which deliver a lubricant to a machine element, such as a bearing in a pump.

The present invention optimizes both equipment and lubricant useful life through identification of parameters that can cause deterioration of the equipment by deterioration of the lubricant.

The system and methods of the present invention are provided for invoking condition monitoring and predicting parametric equipment and lubricant condition among a plurality of machines; relying on individual or multiple machine and or lubricant combinations; comprising establishing a based routine accepting information from multiple sources to simultaneously calculate and compare measured and projected conditions relative to parameters selected to be critical; including multiple condition monitoring techniques like: lubricant analysis, vibration analysis, thermography, ultrasound and equipment lubricant monitoring techniques whereas parameters monitored are variables and a specific parametric value represents condition or a group of variables together represents a condition; said variables are not to be confused with attribute data indicating pass/fail without identifying a specific parametric value. The process outputs the specific parameter and days to exceed specified condemning limit for each combination of equipment and lubricant selected.

The systems and methods of the present invention can utilize simultaneous parametric analysis, condition limit sets specific to equipment/lubricant characteristics, and user specified maintenance time intervals required for planning.

The systems and methods of the present invention can identify time based performance deterioration, immediate deterioration due to situations such as component failure, and common parametric deterioration within a group of equipment or a type of lubricant.

BRIEF DESCRIPTION OF THE DRAWINGS

FIG. 2 is a chart showing components of a typical operating environment to which the methods of the present invention are applied;

FIG. 3 is a chart showing a typical list of manufacturers whose equipment might be present in a typical operating environment to which the methods of the present invention are applied;

FIG. 4 is a chart showing a typical list of lubricants and equipment identifiers present in an exemplary environment;

FIG. 5 is a chart showing a typical list of component types present in an exemplary environment;

FIGS. 7-16 are an example application of the sequence shown in the schematic of FIG. 6 upon an exemplary environment.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Figure 1:
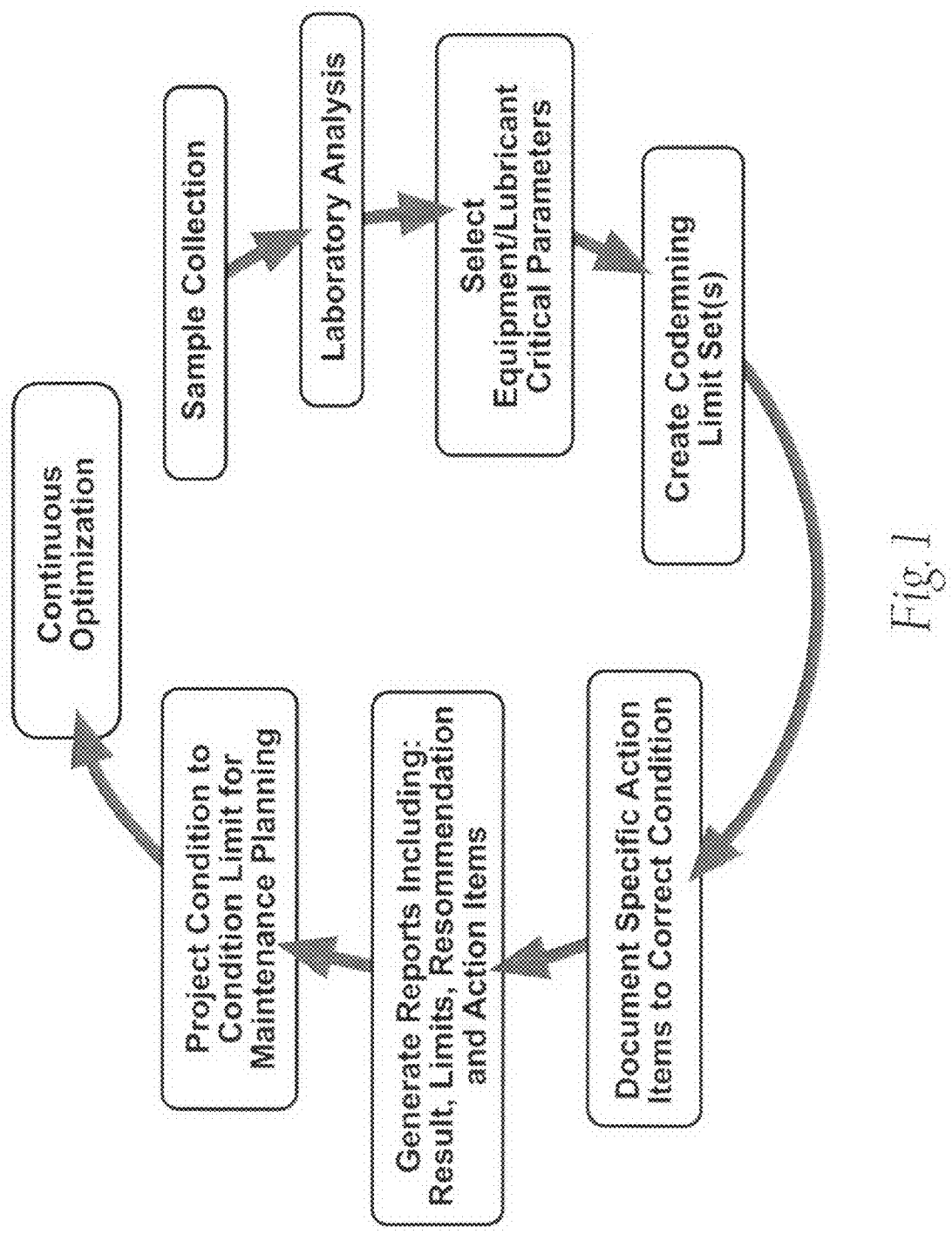
FIG. 1 is a schematic representation of a method for managing and predicting condition of lubricating fluids.

Referring now to FIG. 1, a schematic representation of a method for managing and predicting condition of lubricating fluids is shown.

The methods of the present invention can begin with sample collection as described below.

On-Site Sample or Data Collection

On-site sample or data collection can be performed using standard liquid sample apparatus or sensor outputs, or digital information. The collected sample or data can be then transported or exported to web routines either directly or through multiple paths either electronically or through direct sample/data delivery to laboratory for analysis.

The sample or data set can then be logged into a data acquisition system using bar codes or other automated processes.

Following sample collection, on-site or off-site sample or data analysis can be performed.

On-site data analysis is typically limited to non-ASTM test methods used as screening devices. These analyses are typically used to direct detailed analysis in a controlled laboratory. On-site screening data can be incorporated into database for correlation with industry standardized test methods (i.e. ASTM standards).

The quality and scope of on-site analysis varies and may or may not be of sufficient quality to independently make critical maintenance decisions. Due to data quality and limited testing, using on-site results is typically not used to accurately project future trends.

Off-site or controlled laboratory analysis is required to conduct accurate modeling. The reduced variability and expanded test capability in a controlled laboratory is a critical component of the invention as trends project known conditions; if known conditions are based on questionable or inconsistent results, projections will incorporate a similar level of error. Development of virtual condition limits created from single or multiple sources.

Next, a virtual composite limit set can be maintained or generated specific to single piece of equipment or equipment/lubricant/application combination or group of equipment.

Each equipment/lubricant/application group can be created to generate both individual and group trends, which can identify specific unit performance within the group operating at the extreme condition limit of the group. Preferred equipment/lubricant/applications can then be modified or created for maximum lifecycle value, facilitated through comparison of group trends to individual trends. These trends would not normally be identified relying solely on individual limits.

Additionally, customer parametric limits can be set. One or multiple parametric limits are accepted as the most reliable and applicable to the specific equipment/lubricant combination/application. Customer limit sets can overwrite other parametric limits.

Equipment manufacturer parametric limits, and lubricant supplier parametric limits can also be set without knowing details as to appropriateness to the application.

In the present invention, predicted parametric limits can be calculated individually for each measured parameter. Predicted parametric limits can incorporate multiple values from historical databases. Condition ratings by experienced analysts can be combined with measured values to determine Normal, Marginal or Critical conditions for each combination.

Fixed parametric limits can be selected based on user preference and user experience. Fixed parametric limits are generally applied in the absence of other limit sets.

Next, data analysis must determine if the measured value or values are typical for the parameter being measured. Data is analyzed to determine whether the measured parameter equals, exceeds, or is below the selected parametric limit.

Parametric measured values below or equivalent to a condemning limit and within expected range will not generate an action item, and the parametric measured value is added to the database.

Parameters exceeding the condemning limit will receive additional review both automatically and by experienced personnel. Once a parameter exceeds the condemning limit, a specific action item might be necessary to return condition to normal. If the measured value is significantly below the projected values it indicates a recent maintenance action or possibly a change in lubricant and must be reviewed prior to accepting data into database. Measured values significantly greater than the project value indicate an incorrect sample/data or a problem with the equipment or lubricant. All significant deviations from expected condition trend values indicate changes in operating parameters or equipment or lubricant condition requiring review.

Each parameter can be assigned unique mathematical trend characteristics or weighting factors highlighting criticality to condition or criticality to unite contribution to a complex system (i.e. a sub system of a power plant turbine) as required to match condition characteristic.

Next, a combination or comparison to other combinations is analyzed in a group comparing data characteristics. Preferred equipment/lubricant applications are identified and combined with preferred maintenance practices to achieve and refine standardization in processes and procedure to maximize performance.

Confidences of mathematically calculated trends are determined using standard statistical metrics such as coefficient of determination. Values outside the expected range greater than two standard deviations or causing the trend line confidence coefficient of determination to decrease below selected values will require further analysis using other parameters to determine if measured values can be confirmed as a normally occurring value, if not the sample data set is considered an outlier and must be confirmed by a duplicate sample or an alternate data set.

Parametric analysis and trending are calculated using simultaneous parametric analysis. The overall sample/data condition rating is complex, dependent on one or multiple parameters and weighting factors specific to the equipment/lubricant application; condition rating is typically not dependent on a single measured or calculated value, but on a combination of measured and calculated values and user experience of an expert in the industry.

The invention described expands analysis to include measured values, calculated values, rate of change; condemning limits target maintenance windows and projected values. The invention effectively assimilates and calculates the plurality of information as additional data is added to the database; combining measured, calculated and other input data to identify the specific parameter or parameters requiring immediate attention. These parameters and the time interval specified are organized and presented as one process to identify critical action items leading to work order generation leading to corrective maintenance actions.

Comparing units within a group following this process provides the most complete condition assessment available, limited only by the type of monitoring technologies.

Next, customer defined action items are generated specific to parameter exceeded. Equipment owner input is a critical component of this process as a result input is accepted for each parameter upper alert and alarm, and lower alert and alarm. In addition to each condemning limit, comments aiding in resolving unacceptable conditions are input and are presented throughout the reporting process; as simple as concurring with the measured values or more complex by combining multiple parameters and experience knowledge to aid maintenance personnel in completing repairs.

A real time list of equipment status is maintained and updated with available data.

The risk factors or days to condemning limit are calculated as new data enters through the database. Each parameter can be recalculated updating mathematical trend projections identifying the parameter exceeding the condemning limit in the nearest future.

Using updated mathematical trends combined with the virtual limit set, condition based on single and multiple equipment/lubricant combinations can be predicted. The number of days to condemning limit for each parameter is calculated individually. The intersection of condition trend to condemning limit is calculated relative to time of calculation. Intersections prior to time of calculation are considered over due and assigned a value of zero or less, indicating immediate action required. Parametric trend lines intersecting with condemning limit in the future are assigned a number corresponding to the duration in days required to intersect; using the time specified by the equipment owner a maintenance time window (MTW) is selected to optimize resource planning.

As an example, a power plant scheduled for annual shut down attempts to maximize repairs and upgrades during this time, knowing the existing and projected condition of all monitored equipment aids in the optimization of available resources.

Units with zero value are most at risk and are listed first, values greater than zero are ranked according to their calculated value to intersect condemning limit and are listed in ascending order. Units with zero or values defined by the MTW are presented as a portion relative to the total units within the group. The risk ranking creates the opportunity to focus resources for maximum values.

The ranking of units within a group combined with multiple other measured values and statistics such as: condition rating, unit descriptive informed, last sample event, average measured interval, target measurement interval, measured value, trend calculated values and limiting parameters exceeding limit creates opportunities to identify immediate maintenance action parameter or parameters with in group causing a common problem. Identifying the future risk condition of each equipment/lubricant combination, is a feature expanding beyond the current condition to include rate of change; a parameter sufficiently complex requiring computer calculation. One can compare multiple parameters further expanding the calculation for each parameter trend requiring advanced complex capability to support real time semi-continuous calculations keeping the databases updated.

Referring now to FIG. 2, application of the present method to a typical operating environment is shown. As can be seen, in a typical operating environment such as the one profiled in FIG. 2, a large number of SPIDs (Service Profile Identifier—SPID) can be present. In the displayed environment, 1014 SPIDS are shown reflecting 49 components. Note that this environment is for illustrative purposes only, to describe operation of the methods of the present invention, and that far different operating environments may be present or acted upon.

Figure 3:
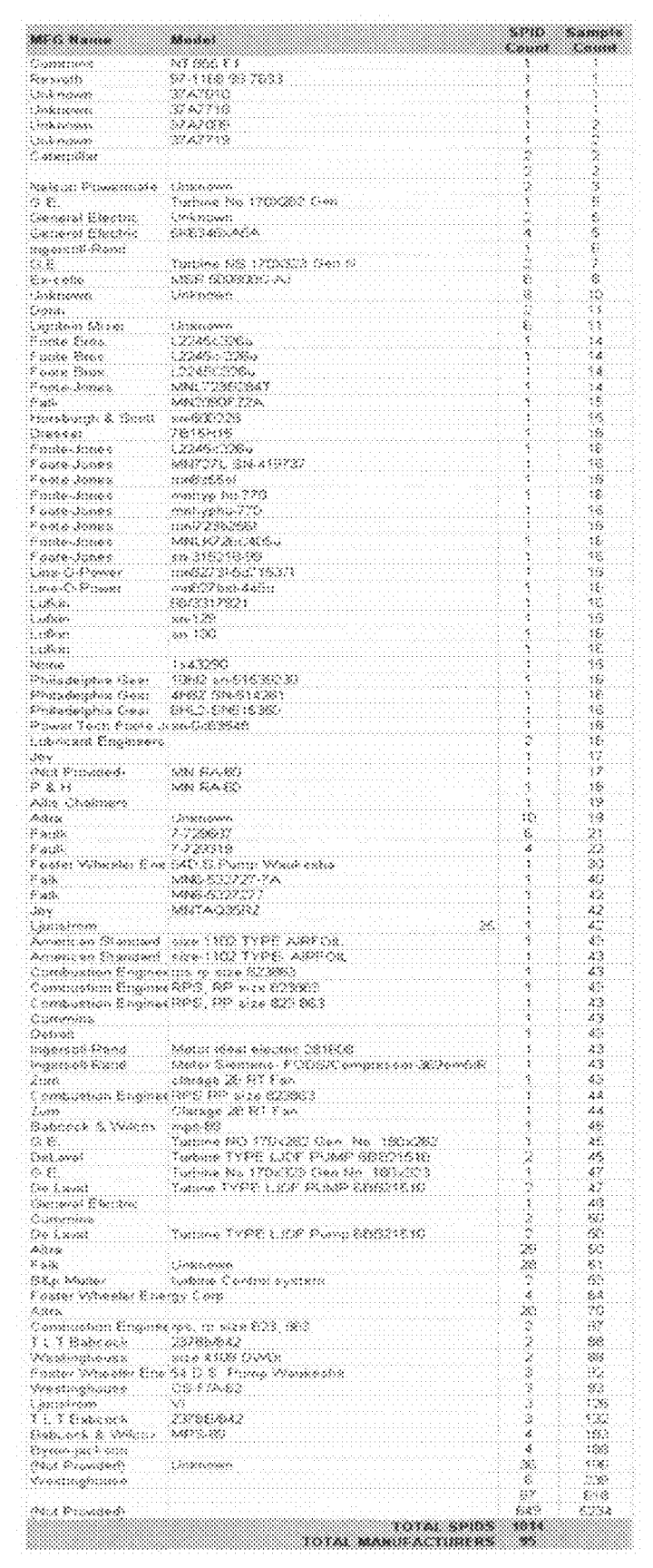

Referring now to FIG. 3, unique manufacturers reflective of the environments of FIG. 2 are shown. In this case, 1014 SPIDS represent equipment from 95 manufacturers.

Figure 4:
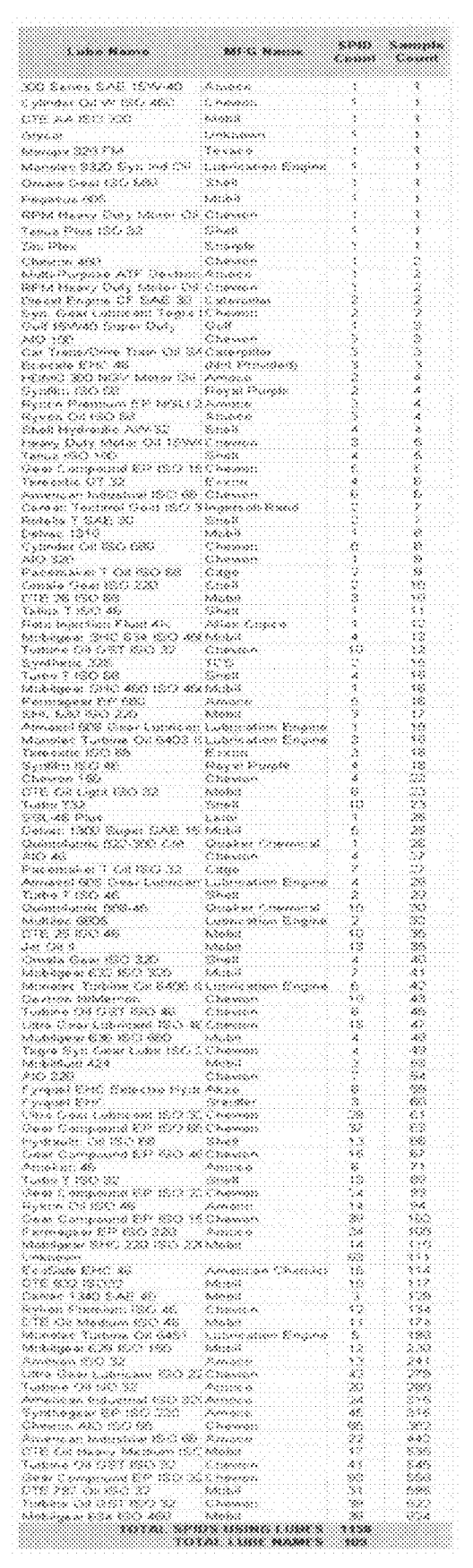

Referring now to FIG. 4, it is seen from the exemplary environment that 1158 SPIDS representing 1098 lubricants are present. The apparatus and methods of the present invention are capable of effectively managing the complexity of 1014 SPIDS' representing 49 component groups, each with unique wear and lubricant characteristics. Each component group can include 25 to 50 individual parameters analyzed for each unit.

In the present method, component groups are created of "like" equipment/lubricant, which allows customization of condition limits that can accurately identify high risk units and common parametric problems in the population. Advanced identification aids in planning and maintenance resource optimization. Groups are preferably be limited to like components and a single or similar lubricant. Properly selecting groups maximizes available information and customer value.

Referring now to FIG. 5, an exemplar of existing equipment grouping and limit set application is shown. In the present method, suggested components in a limit set are grouped by similar characteristics (i.e. separate turbines from gear reducers). The expected result with this limit set will be consistent alarms on normal conditions for some equipment/lubricants (e.g., gearbox-high wear debris is normal) and never an alarm on abnormal condition (e.g., turbine-extremely low wear debris). Because improper alarms misdirect maintenance resources and increase risk of failure, improper alarms are not desirable.

Figure 6:
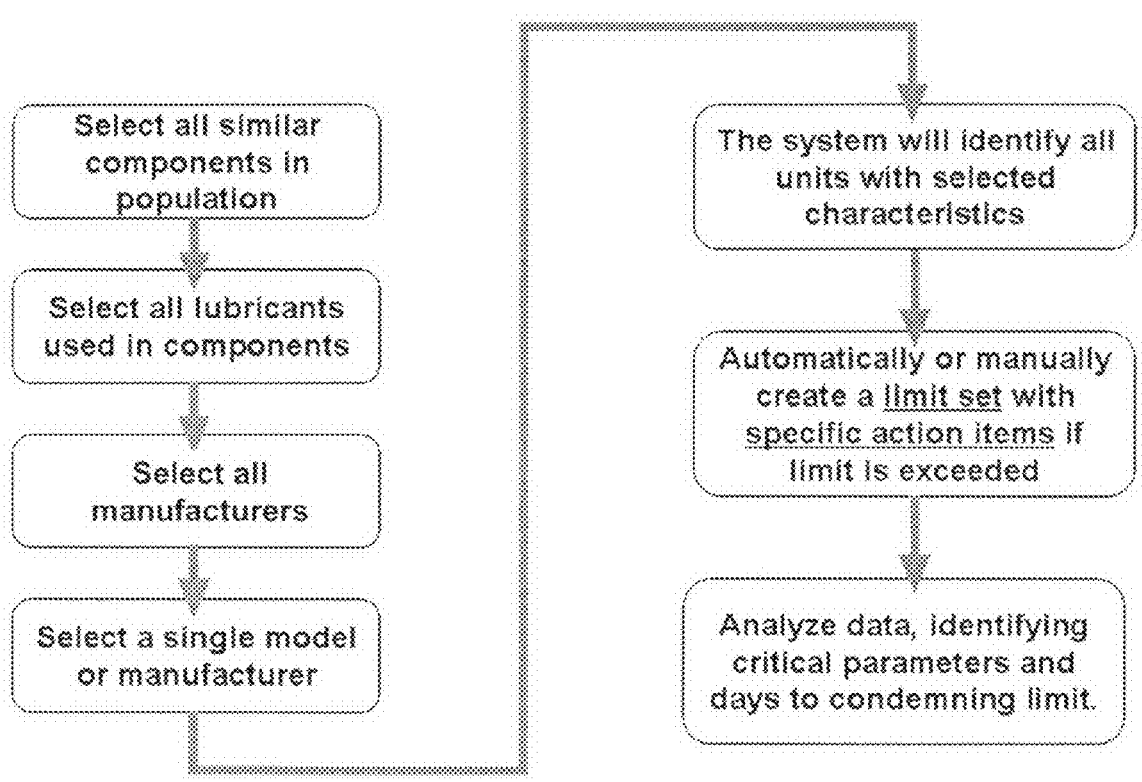
FIG. 6 is a schematic showing the steps in order analyze data, identifying critical parameters and days to condemning limit.

Referring now to FIG. 6, a schematic approach to analyze data, identifying critical parameters and days to condemning limit is shown. Preferably, all similar components in population are selected. Next, all lubricants used in components are selected. Next, all manufacturers are selected. Next, a single model or manufacturer is selected, and the system identifies all units with selected characteristics. Next, a limit set is automatically or manually created with specific action items if limits are exceeded. Next, data are analyzed to identify critical parameters and days to condemning limit.

The sequence shown in the schematic of FIG. 6 is shown in FIGS. 7-16. In FIG. 7, all similar components in population are selected, and preferably limited to like components and a single or similar lubricant. Properly selecting groups maximizes available information and customer value.

Figure 8:
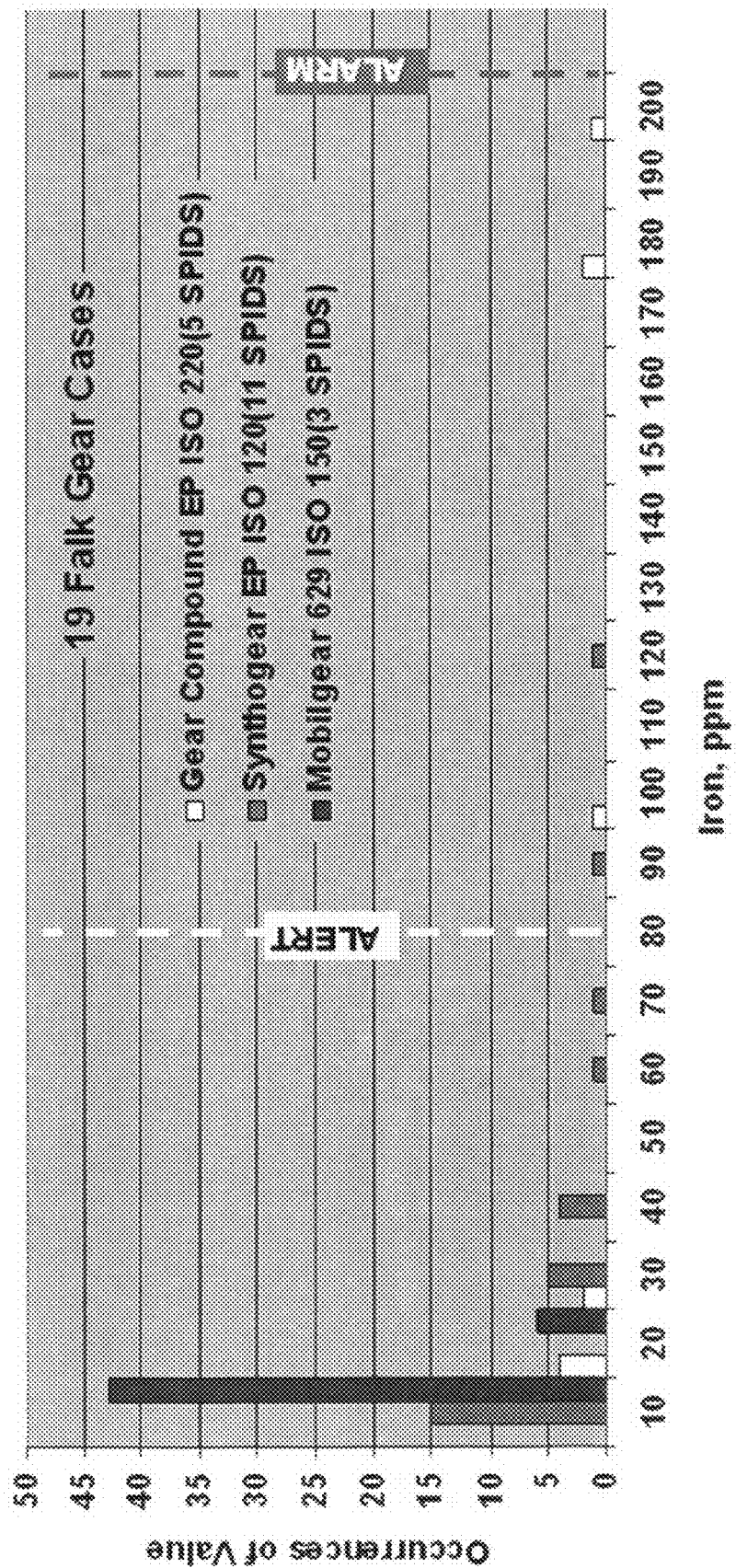

In FIG. 8, following group selection, lubricants used in components are selected. In the illustrated, the number of occurrences for each of the three lubricants identifies significant differences. Possible parameters affecting difference include sample interval, maintenance practices or lubricant quality. In the illustrated example the observation is shown limited to Iron: Mobilgear-sample interval and time in service can be extended with minimum risk resulting in increased overall value. In the illustrated example, a single parameter analysis for iron is shown; however, multiple parameter analysis can be performed, for instance if iron is not be controlling parameter.

Figure 9:
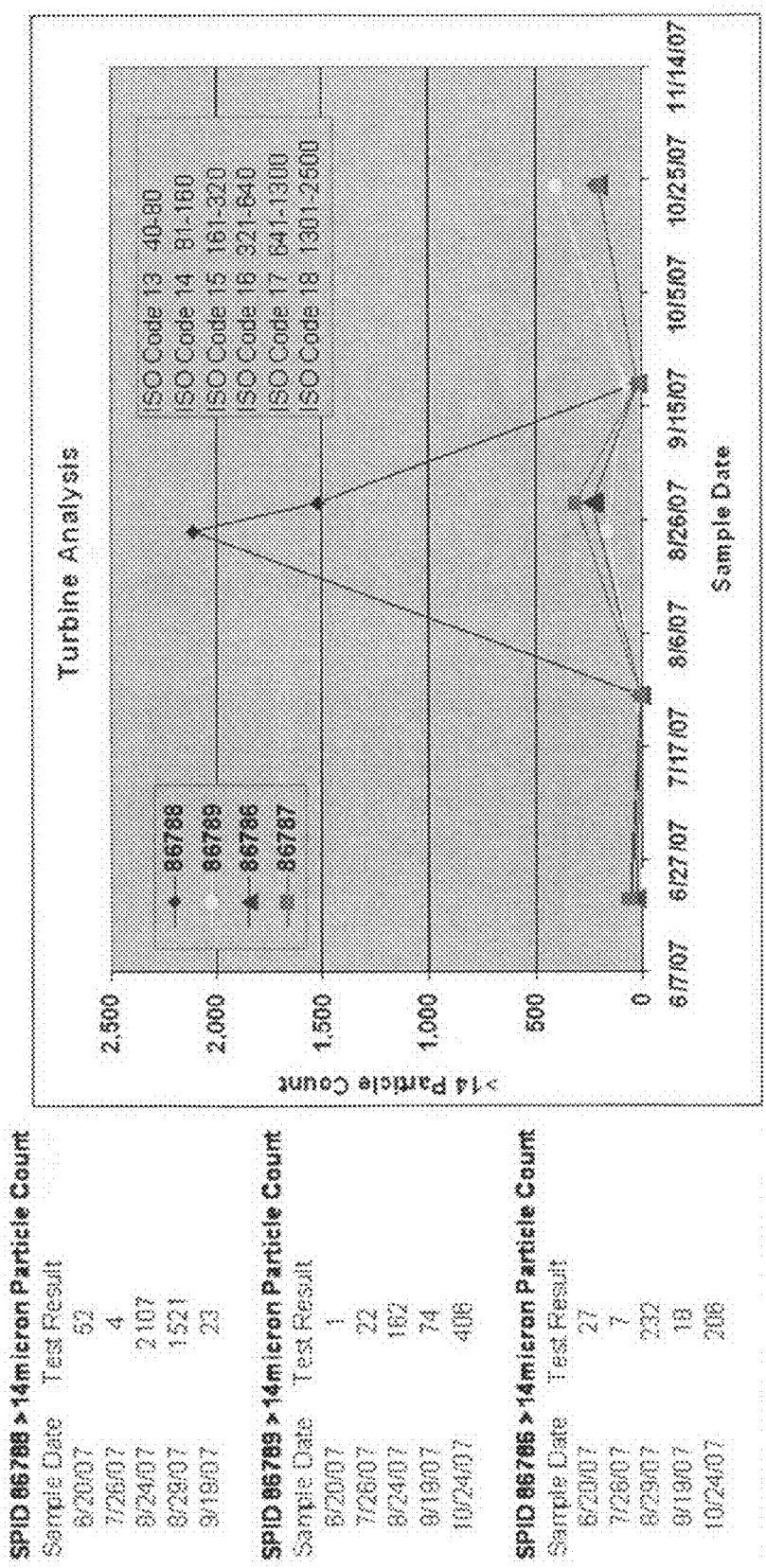

In FIG. 9, following group selection, lubricants used in components are selected and in this example, particle count data >14 micron is the controlling critical parameter for SPID 86788. Correcting the high particle count will return all results to typical values for the Turbine/DTE 797 Oil ISO 32 group. Possible Maintenance action is noted for SPID 86788 at values of 2107, 1521, and 23.

Referring now to FIG. 10, a SPID limit set report is shown. Multiple limits can set for the selected group.

Figure 11:
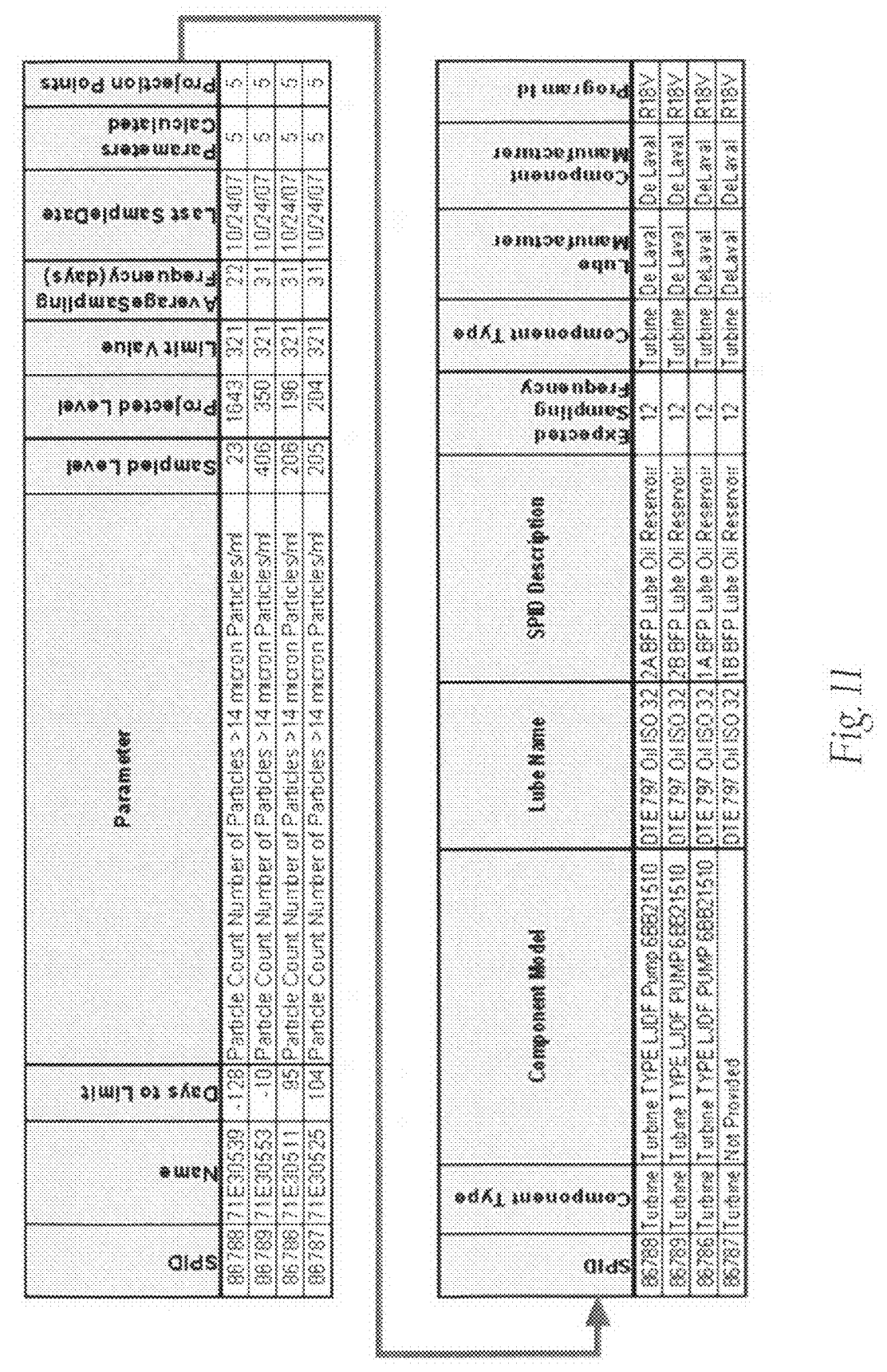

Referring now to FIG. 11, an analysis identifying days to condemning limit based on critical parameters and available data is shown. Knowledge of maintenance action decreasing sampled value for SPID 86788 would adjust value. Expanding or adjusting limits can effectively identify the critical parameter reaching condemning limit first. In this example, the limit set applied identified >14 micron as the controlling parameter.

Referring now to FIGS. 12a and 12b, total lubricants in gear cases and gear case types with a single component analysis desired (highlighting the single Foote-Jones gear cases). After selecting the single component, single manufacturer shown in FIGS. 13a and 13b, the exemplary Foote-Jones Gear Cases, Limits and Recommendations as shown in FIG. 14 can be generated to control the Rating and Suggested Action Items in the Condition Reports. Limits are preferably created automatically or manually resulting in high value maintenance actions.

Referring now to FIG. 15, a data projection for equipment condition is shown. In this example, out of the total of 9 projections and for the service interval of 90 days, 3 (33.33%) of units will reach a condemning limit before the end of service interval and may require a maintenance action, 6 (66.67%) of units will not reach a condemning limit before the end of service interval and do not require a maintenance action.

Selecting effective limits identifies units at highest risk of failure, identifies units exceeding limits and provides recommended action item, creates the opportunity to take effective action immediately when limit is exceeded, and creates the opportunity to plan condition maintenance.

Figure 16A:
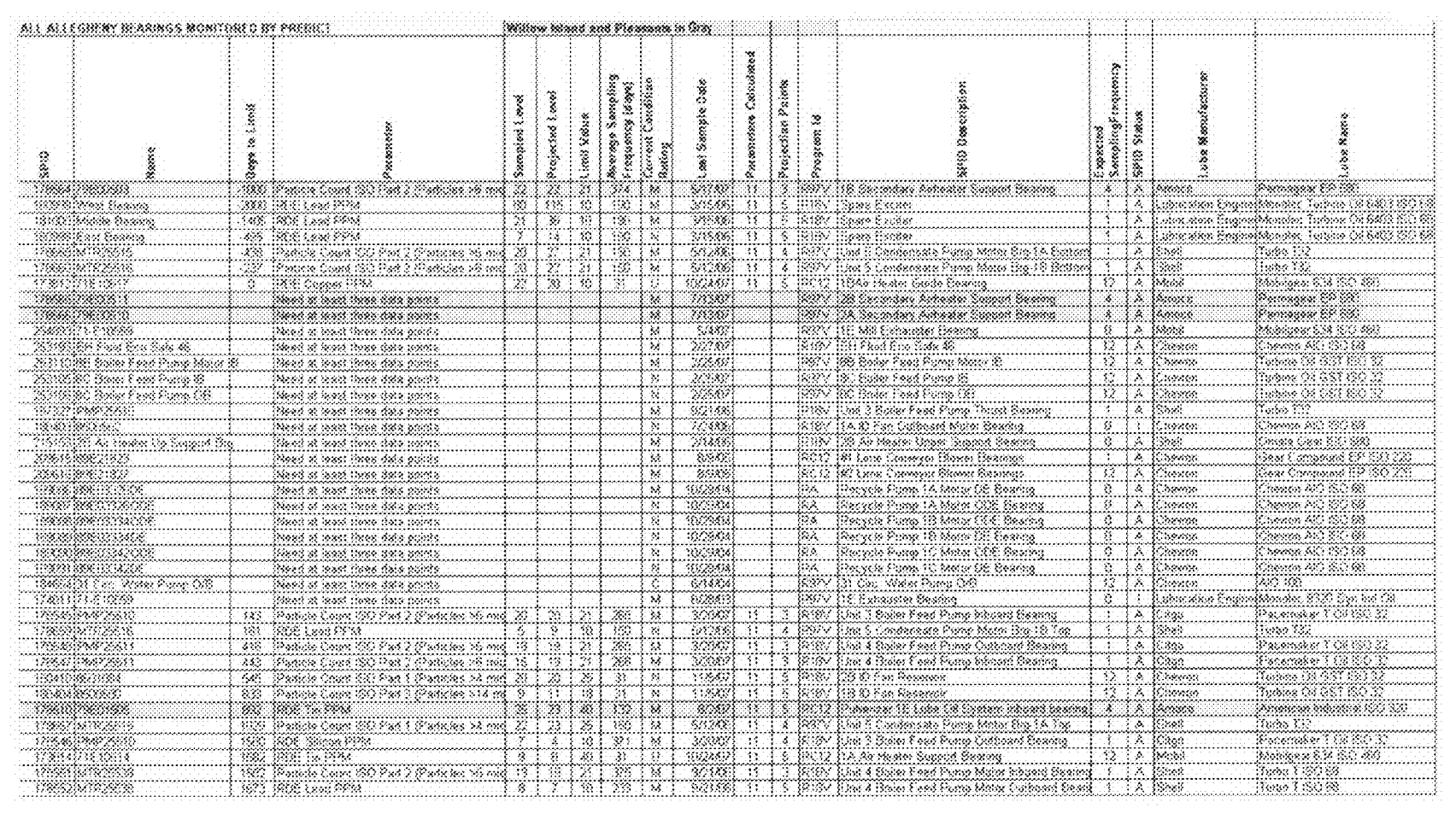
Figure 16B:
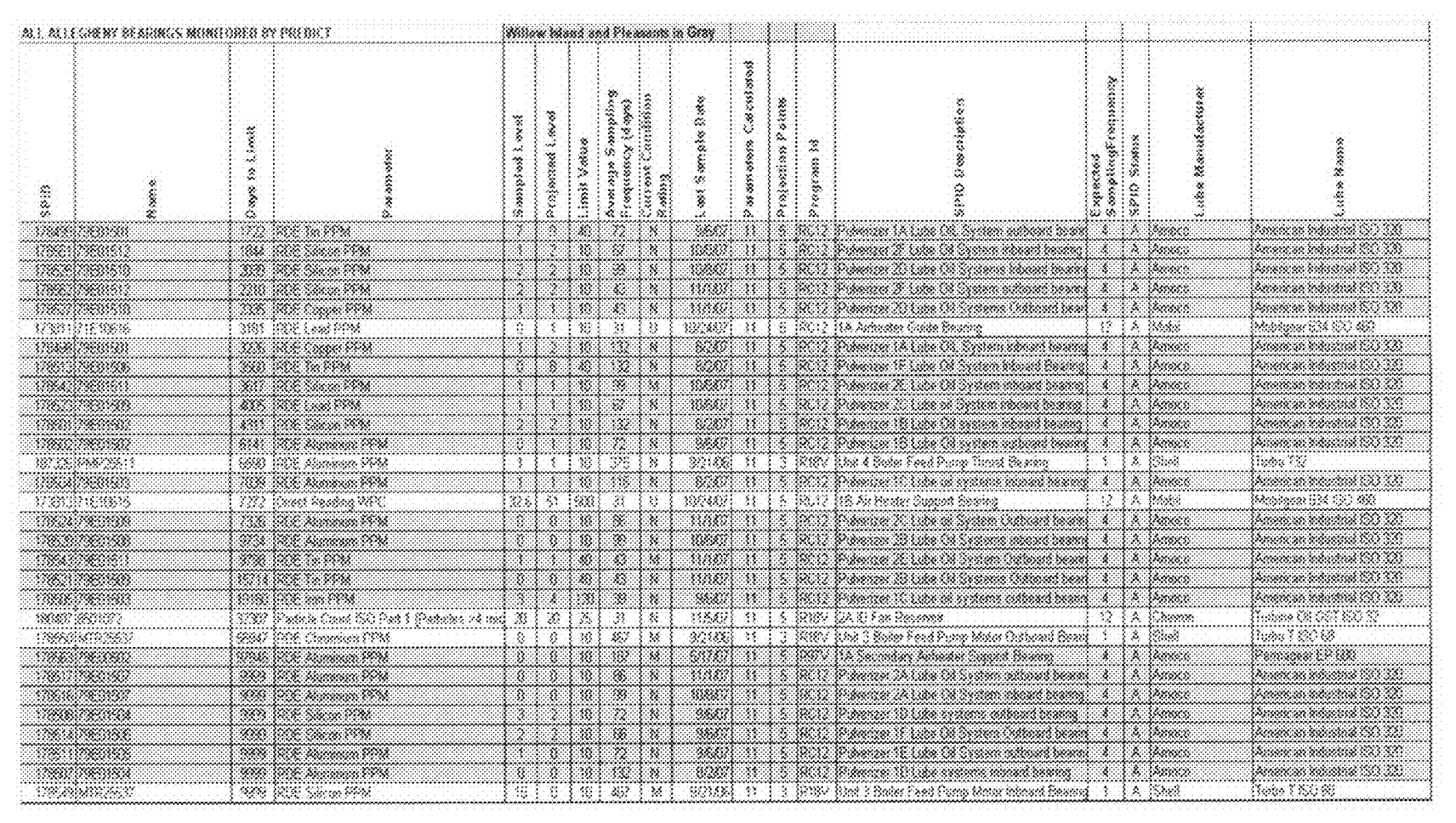

Referring now to FIGS. 16a and 16b, comparisons are shown between all bearings, highlighting differences in: condition as indicated by days to limit, sample activity and availability of data. Highlighting SPIDS from one facility relative to others demonstrates general condition differences between facilities. Differences are likely due to multiple issues including differences in lubricants.

Grouping like equipment and lubricants can reveal lubricant consolidation opportunities, the affect of sampling interval, maintenance practices and lubricant quality and strategies to optimize, display how to identify common parameter affecting multiple equipment in a group, how to use equipment owner limits and recommendations through out the analysis and rating process, identify maintenance planning opportunities, and reveal an opportunity to standardize maintenance process and condition management throughout all facilities.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

I claim:

1. A method of managing and predicting condition of a lubricant, the method comprising:
    selecting similar components in a population of diverse equipment requiring lubricant;
    collecting a sample of a lubricant from at least one of said similar components in said population of diverse equipment requiring lubricant;
    analyzing said lubricant for a plurality of analytes;
    selecting critical parameters for said lubricant;
    creating a condemning limit set for said analytes;
    correcting a condition approaching or exceeding said condemning limit set;
    generating a report comprising at least one of a result, a limit, a recommendation or an action item;
    projecting conditions of said analytes to a time when said conditions will equal said condemning limit across all of said similar components in said population of diverse equipment requiring lubricant;
    ranking unit equipment risk relative to a parametric condition and said condemning limit.

* * * * *